(12) United States Patent
Daage et al.

(10) Patent No.: US 6,624,204 B1
(45) Date of Patent: *Sep. 23, 2003

(54) CARBON MONOXIDE HYDROGENATION PROCESS

(75) Inventors: Michel A. Daage; Russell John Koveal; David Chester Long; Leroy Russell Clavenna, all of Baton Rouge, LA (US); Trikur Anantharaman Ramanarayaman, Somerset; James Dirickson Mumford, Long Valley, both of NJ (US); Claude Clarence Culross, Baton Rouge, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,914

(22) Filed: Sep. 1, 2000

(51) Int. Cl.⁷ .......................... C07C 27/00; B01J 20/34; B01J 25/00; B01J 23/40; B01J 23/72
(52) U.S. Cl. .................. 518/709; 518/700; 518/715; 502/20; 502/301; 502/326; 502/331
(58) Field of Search ................. 518/700, 709, 518/715; 502/20, 326, 331, 301

(56) References Cited

U.S. PATENT DOCUMENTS

| | | | |
|---|---|---|---|
| 2,583,619 A | 1/1952 | White ................... | 252/477 |
| 3,661,798 A | 5/1972 | Cosyns et al. .......... | 252/416 |
| 4,089,812 A | 5/1978 | O'Hare et al. .......... | 252/466 |
| 4,399,234 A | 8/1983 | Beuther et al. ......... | 518/715 |
| 4,492,774 A | 1/1985 | Kibby et al. ........... | 518/713 |
| 4,585,798 A | 4/1986 | Beuther et al. ......... | 518/715 |
| 4,670,414 A | 6/1987 | Kobylinski et al. ..... | 502/174 |
| 4,826,799 A * | 5/1989 | Cheng et al. ........... | 502/301 |
| 4,895,994 A * | 1/1990 | Cheng et al. ........... | 585/270 |
| 4,910,175 A | 3/1990 | Michel et al. .......... | 502/24 |
| 4,977,126 A | 12/1990 | Mauldin et al. ........ | 502/242 |
| 5,168,091 A | 12/1992 | Behrmann et al. ...... | 502/325 |
| 5,260,239 A | 11/1993 | Hsia ....................... | 502/30 |
| 5,268,344 A | 12/1993 | Pedrick et al. ......... | 502/30 |
| 5,283,216 A | 2/1994 | Mitchell ................. | 502/30 |
| 5,292,705 A | 3/1994 | Mitchell ................. | 502/325 |
| 5,348,982 A | 9/1994 | Herbolzheimer et al. | 518/700 |
| 5,382,748 A | 1/1995 | Behrmann et al. ...... | 585/899 |
| 5,536,694 A * | 7/1996 | Schuetz et al. ......... | 502/301 |
| 5,973,012 A | 10/1999 | Behrmann et al. ...... | 518/700 |

FOREIGN PATENT DOCUMENTS

| | | | |
|---|---|---|---|
| EP | 0253924 | 7/1986 | ............ B01J/23/74 |
| GB | 655827 | 8/1951 | |

OTHER PUBLICATIONS

Suslick et al., "Sonochemical Synthesis of Amorphous Iron", *Nature*, vol. 353, pp. 414–416 (1991).

Gibson et al., "Synthesis and Characterization of Anisometric Cobalt Nanoclusters", *Science*, vol. 267, pp. 1338–1340 (1995).

Potoczna–Petru et al., "Influence of Oxidation–Reduction Treatment on the Microstructure of $Co/SiO_2$ Catalyst", *Applied Catalysis A*, General pp. 113–120 (1998).

Savelov et al., "Role of Alloying Metals in Raney Ni, Co, and Cu Catalysts", *Russian Journal of Physical Chemistry*, vol. 62(11) pp. 1537–1540 (1988).

\* cited by examiner

*Primary Examiner*—J. Parsa
(74) *Attorney, Agent, or Firm*—Estelle C. Bakun

(57) ABSTRACT

A method is disclosed for renewing the activity of a Dispersed Active Metal (DAM) catalyst during operation of a reactor wherein the hydrogenation of carbon monoxide to produce a mixture of hydrocarbons is being carried out comprising withdrawing a mixture of hydrocarbons and a portion of the DAM catalyst, reducing the hydrocarbon content thereof, heating the mixture above the melting temperature of at least one of the metals of the DAM to form a melt, removing any slag that forms on the melt, cooling the melt to form a solid, reducing the particle size thereof to form a renewed particulate DAM catalyst, which is then returned to the reactor. Wherein the DAM catalyst is a Raney catalyst, a leachable metal is added to the reduced hydrocarbon mixture or the melt under non-oxidizing conditions and, after the solid is reduced to a fine particle size, extracting the leachable metal with caustic. The activity of the DAM may be modified or enhanced during the process by the addition of promoter metals, or prior to being returned to the reactor, by slurry low temperature oxidation followed by reduction at elevated temperature, and may further be enhanced by being passivated prior to being returned to the reactor. The catalyst may be withdrawn and replaced periodically or continuously during the operation of the reactor.

31 Claims, No Drawings

CARBON MONOXIDE HYDROGENATION PROCESS

This invention relates to the production of higher hydrocarbons from synthesis as utilizing Dispersed Active Metal catalysts comprising one or more Group VIII metals.

BACKGROUND OF THE INVENTION

The production of higher hydrocarbon materials from synthesis gas, i.e. carbon monoxide and hydrogen, commonly known as the Fischer-Tropsch process, has been in commercial use for many years. In such processes, the synthesis as mixture is contacted with a suitable Fischer-Tropsch catalyst under shifting or non-shifting conditions, preferably the latter, wherein little or no water gas shift takes place. Suitable Fischer-Tropsch catalysts comprise one or more Group VIII catalytic metals, such as iron, cobalt and nickel.

There exist many variations of the basic preparation of Fischer-Tropsch catalysts such as, for example, deposition of alloys onto a preformed support by flame spraying. (U.S. Pat. No. 4,089,812), formation of the alloy by surface diffusion of aluminum on a non-leachable metal substrate (U.S. Pat. No. 2,583,619), and forming pellets from the powdered alloys for use in fixed bed reaction vessels (U.S. Pat. No. 4,826,799, U.S. Pat. No. 4,895,994 and U.S. Pat. No. 5,536,694, for example). The choice of a particular catalyst formulation, method of fabrication and method of activation depends in large measure on the catalytic activity, the desired product or products, whether or not the catalyst can be regenerated and the specific process components and configurations.

The production of hydrocarbons by the Fisher-Tropsch process may be carried out in virtually any type reactor, e.g. fixed bed, moving bed, fluidized bed, slurry, bubbling bed and the like. A preferred reactor carrying out such reactions is the slurry bubble column developed by Exxon Research & Engineering Company. This reactor, which is ideally suited for carrying out highly exothermic, three-phase catalytic reactions, is described in U.S. Pat. No. 5,348,982. In such reactors, the solid phase catalyst is dispersed or held in suspension in a liquid phase by a gas phase, which continuously bubbles through the liquid phase. The catalyst loading in slurry bubble reactors can vary within a broad range of concentrations, but must remain short of the so-termed "mud limit" where the concentration of the catalyst reaches a level such that mixing and pumping of the slurry become so difficult that practical operation is no longer possible. The use of high metal-loading catalysts or bulk metal catalysts is preferred in slurry bubble reactors in order to maximize the productivity of both catalyst and reactor.

Particularly suited for the production of hydrocarbons by Fischer-Tropsch synthesis from synthesis gas are Dispersed Active Metals ("DAM") which are primarily, i.e. at least about 50 wt. %, preferably at least 80 wt. %, composed of one or a mixture of metals such as described above and are, without further treatment, capable of catalyzing Fischer-Tropsch synthesis. DAM catalysts may be prepared by any of a number of art-recognized processes. An extensive review of process of forming DAM catalysts can be found in "Active Metals", Edited by Alois Furstner, published by VCH Verlagsgesellschaft mbH, D-69451 Weinheim (FRG) in 1996 and the references cited therein. Methodologies described therein include the Rieke method, the use of ultrasound, reduction of metal salts, colloids, nanoscale cluster and powders. Other relevant references include, for example, the preparation of amorphous iron catalyst by high intensity sonolysis of iron pentacarbonyl, Suslick et al. Nature, Vol. 353, pp 414–416 (1991) and the formation of single domain cobalt clusters by reduction of a cobalt salt with hydrazine, Gibson et el., Science, Vol. 267, pp 1338–1340, (1998). Finally, intermetallic alloys, particularly those known for forming metal hydrides, such as $LaCo_5$, can be formed into a fine powder by the application of hydrogen adsorption/desorption cycles. DAM catalysts can also be prepared by thermal or chemical decomposition of metal formates or oxalates. These methods are given as examples and are not intended in any way to limit the term "DAM" as utilized in the context of the present invention.

There are many well-known methods for the preparation of DAM catalysts in the literature. In 1924, M. Raney prepared a Nickel hydrogenation catalyst by using a process known today as the Raney Process and Raney catalysts. Such catalysts are described and illustrated, for example, in U.S. Pat. No. 4,826,799. The process of preparing these catalysts is, in essence, forming at least a binary alloy of metals, at least one of which can be extracted, and extracting it leaving a porous residue of the non-soluble metal or metals that possesses catalytic activity. These groups of metals are well known to those skilled in the art. The residue catalyst metals include Ni, Co, Cu, Fe and the Group VIII noble metals. The leachable or soluble metal group includes aluminum, zinc, titanium or silicon, typically aluminum. Once the alloys are formed, they are ground to a fine powder and treated to extract the leachable metal, typically with strong caustic, such as sodium hydroxide. Alternatively, the alloy is formed onto or impregnated into a suitable rigid support structure which is then extracted with caustic to form a porous, supported catalyst.

The high metal content of DAM catalysts, i.e. at least 50% metal, represents a major economic impediment to their use unless low cost recovery technology can he implemented as well. Those of ordinary skill in the art are aware that metals constituting DAM catalysts, particularly Raney catalysts, are conventionally recovered by subjecting the used, or spent catalysts to multiple processing steps, principally for the purpose of purification of the metal. The particular methodology chosen to purify and recover the metal depends in large measure on the nature of the impurities and contaminants that have been deposited on the catalyst during use. In most applications, drastic treatments are required because of significant contamination of the metals by one or more of carbonaceous deposits, heteroorganic compounds, i.e. compounds containing sulfur and/or nitrogen, and other metals.

Typically, spent DAM catalysts are treated in the reactor by oxidation to permit safe unloading and shipping to a metal processing facility. The oxidation can be carried out, for example, by air oxidation of the catalyst slurry, or by treatment with bleach as recommended by catalyst manufacturers. In the metal processing facility, the catalysts are generally roasted in air, dissolved in strong acid and the different metals selectively reprecipitated in the form of salts. The metals may be reused in the form of the salts, or converted back into metallic form, depending on the requirements of the synthesis. Such treatments must be effective and efficient because, although carbon monoxide hydrogenation processes are conducted in an exceptionally clean environments DAM catalysts are generally sensitive to comparatively minor amounts of contaminants.

Those of ordinary skill in the art recognize that the economic worth of a given catalyst is a function of its original cost, its value as a spent catalyst, e.g. for regeneration of fresh catalyst, its activity and its half-life in the reactor. Likewise, it will be appreciated that a process that will effectively extend the useful life of a catalyst before it must be disposed of through conventional metal recovery will significantly improve the value of that catalyst. Such a process is provided in accordance with the present invention.

SUMMARY OF THE INVENTION

In accordance with the present invention, there is provided a significant improvement in the catalytic hydrogenation of carbon monoxide to form a mixture of hydrocarbons in a reactor wherein the catalyst is a Dispersed Metal Catalyst and is not immobilized comprising, during operation of the reactor to produce said hydrocarbons, withdrawing a mixture of hydrocarbons and a portion of the catalyst, reducing the hydrocarbon content thereof, heating the resulting mixture in a non-oxidizing atmosphere to a temperature above the melting temperature of at least one of the metals, thereby substantially removing non-metallic impurities therefrom and forming a slag of any refractory metal oxides therein, removing the slag, if present, cooling the melt to solidify it, treating the solid to reduce the particle size thereof to a fine powder of renewed catalyst, preferably by a series of hydrogen absorption/desorption cycles, and returning the catalyst to the reactor. The mixture withdrawn from the reactor may be physically separated by size of the catalyst particles and only the fine particles treated in accordance with the process of the invention.

In another embodiment of the invention, the DAM catalyst is a Raney catalyst and a leachable metal is added to the reduced hydrocarbon mixture, or the melt, under non-oxidizing conditions and, after the melt has been allowed to solidify and the solid reduced to a fine particle size by physical comminuting the leachable metal is extracted with caustic to yield renewed catalyst particles.

In a further embodiment, the activity of the DAM catalyst may be modified during the process by the addition to the melt, or the reduced hydrocarbon mixture, of one or more metals that promote the catalytic activity of the DAM. In another embodiment, the activity of the DAM, or the DAM modified as above, may be further enhanced by partial oxidization in a slurry at low temperatures to form an oxidized precursor which is subsequently activated by reduction with hydrogen as at elevated temperature to reform the catalyst. In a still further embodiment, the renewed or enhanced DAM may be passivated prior to reintroduction into the reactor by treatment with carbon monoxide or carbon monoxide and hydrogen under conditions such that will prevent significant decomposition or hydrogenation, respectively, of the carbon monoxide. In any of the embodiments described above, the hydrocarbon/catalyst mixture may be periodically or continuously withdrawn from and replaced into the reactor.

DETAILED DESCRIPTION OF THE INVENTION

Dispersed Active Metals (DAM), which correspond essentially to reduced metals, are utilized in a broad range of applications such as hydrogenation of fats and specialty chemicals. Start-up procedures, which may include specific activation sequences, are highly dependent upon the catalytic reaction, the process design and, in particular, the reaction vessel design and configuration. The slurry bubble column discussed above, is a preferred vessel for carrying out carbon monoxide hydrogenation reactions and also for the process of catalyst renewal or enhancement of the present invention. In such reactors, the solid phase catalyst is dispersed or held in suspension in a liquid hydrocarbon phase by a gas phase, which continuously bubbles through the liquid phase. DAM catalysts useful for such applications contain at least 50 wt. %, preferably at least 80 wt. %, of metal catalysts in the reduced metallic form. Preferred catalysts include intermetallic alloys or Raney catalysts, for example Raney cobalt. Among the intermetallic alloys, preferred examples are those suitable for forming metal hydrides, such as $LaCo_5$. Most preferably, the DAM catalyst comprises one or more of Co, Ru, Fe and Cu.

Catalysts most suited for use in slurry column reactors vessels, typically are in a finely particulate form having an average diameter ranging from 1 to 1,000 1 m, preferably from 10 to 500 1 m, most preferably from 20 to 100 1 m. The use of high metal loading catalysts and/or bulk catalysts is preferred in order to maximize the productivity of the reaction vessel. The present process may be applied to other conventional reaction vessels known in the art wherein the catalyst is not immobilized, such as fluidized bed, slurry, bubbling bed and the like. In such moving bed reactors contaminated catalyst would typically be withdrawn from the bottom of the vessel and catalyst that had been renewed or enhanced in accordance with the present process would be replaced at the top.

In the carbon monoxide hydrogenation reaction, a syngas comprising a mixture of hydrogen and carbon monoxide is bubbled up into the reactive hydrocarbon-containing slurry in which it is catalytically converted into liquid and gaseous products, preferably liquid hydrocarbons, with shifting or non-shifting conditions, preferably the latter, wherein little or no water gas shift takes place. This hydrocarbon synthesis ("HCS") process is generally carried out at temperatures of from about 160° C. to 260° C., pressures of from about 5 atm to about 100 atm, preferably from 10 atm to 40 atm, and gas space velocities of from about 300V/Hr/V to about 20,000V/Hr/V, preferably from about 1,000V/Hr/V to about 15,000V/Hr/V. The stoichiometric ratio of hydrogen to carbon monoxide is about 2.1:1 for the production of higher hydrocarbons. This ratio can vary from about 1:1 to 4:1, preferably from 1.5:1 to 2.5:1, more preferably from 1.8:1 to 2.2:1. These reaction conditions are well known to those skilled in the art and a particular set of reaction conditions can readily be determined from the parameters given herein. The hydrocarbon-containing products formed in the process are essentially free of sulfur and nitrogen-containing contaminants.

The hydrocarbons produced in a process as described above are typically upgraded to more valuable products by subjecting all or a portion of the C5+ hydrocarbons to fractionation and/or conversion. By "conversion" is meant one or more operations in which the molecular structure of at least a portion of the hydrocarbon is changed and includes both non-catalytic processing, e.g. steam cracking, and catalytic processing, e.g. catalytic cracking, in which the portion, or fraction, is contacted with a suitable catalyst. If hydrogen is present as a reactant, such process steps are typically referred to as hydroconversion and variously as hydroisomerization, hydrocracking, hydrodewaxing, hydrorefining and the like. More rigorous hydrorefining is typically referred to as hydrotreating. These reactions are conducted under conditions well documented in the literature for the hydroconversion of hydrocarbon feeds, including hydrocarbon feeds rich in paraffins. Illustrative, but non-limiting, examples of more valuable products from such feeds by these processes include synthetic crude oil, liquid fuel, emulsions, purified olefins, solvents, monomers or polymers, lubricant oils, medicinal oils, waxy hydrocarbons, various nitrogen- or oxygen-containing products and the like. Examples of liquid fuels includes gasoline, diesel fuel and jet fuel, while lubricating oil includes automotive oil, jet oil, turbine oil and the like. Industrial oils include well drilling fluids, agricultural oils, heat transfer oils and the like.

Typical Fisher-Tropsch HCS reaction conditions effective to form hydrocarbons comprising mostly C5+ paraffins, (for example C5+–C200 and preferably C10+ paraffins) in a slurry HCS process employing a catalyst comprising a cobalt component include, for example, temperatures, pressures and gas hourly space velocities in the range of from about 160–260° C., 5–40 atm. and 100–40,000V/hr/V, expressed as standard volumes of the gaseous carbon monoxide and hydrogen mixtures (25° C., 1 atm.) per hour per volume of catalyst, respectively. The syngas utilized in carbon monoxide hydrogenation may be formed by various means known to those of ordinary skill in the art, such as a fluid bed syngas generating unit as is disclosed, for example, in U.S. Pat. Nos. 4,888,131, and 5,160,456. Regardless of the source, syngas typically may contain chemical species, such as ammonia and hydrogen cyanide, that will, over time, cause deactivation of the catalyst. Other deactivating chemical species may be formed during the carbon monoxide hydrogenation process itself. Those skilled in the art are aware of the fact that deactivation by those contaminants is generally reversible and the catalyst can be renewed by treatment with hydrogen. However, catalyst deactivation that cannot be renewed may be caused by the formation of refractory carbonaceous residues and/or permanent poisons such as sulfur, phosphorus, halides and other metal contaminants.

In accordance with the present invention, the HCS process is enhanced by a process that renews the catalyst during operation of the reactor. The process is commenced by the withdrawal from the reactor of a mixture of hydrocarbon, typically molten wax, and a portion of the catalyst. While the amount of catalyst removed can vary within a wide range, those of ordinary skill in the art will appreciate that it is necessary that sufficient catalyst remain in the reactor to sustain the desired level of production. Generally, from about 0.01 wt. % to about 10 wt. % of the catalyst will be withdrawn from the reactor at a given point in time during production. It is not intended that such amount of catalyst be removed in a single quantity. Rather, portions of the withdrawn catalyst will be at various stages of the process of the invention at any given time so that, when a portion is returned to the reactor, an estimated like amount can be withdrawn. It is also contemplated within the present invention to continuously withdraw and replace catalyst while the reactor is in production. Further, since a reactor will typically run for a considerable period of time before sufficient contaminants accumulate to require implementing the subject process, after it is calculated that substantially all of the catalyst in a reactor has been treated in accordance with the present process, it may again be operated for a like period of time before re-commencing the treatment. In this manner, it is possible to operate a reactor for extended periods of time before it would have to be shut down for normal maintenance and the like, a considerable economic advantage. While it would be possible to stop the reactor to carry out the process of the invention, there would be no practical merit in doing so since it can be effectively carried out during production.

The hydrocarbon content of the mixture withdrawn from the reactor is essentially similar to that of the reactor at the mixture collection port. Those skilled in the art will recognize that the hydrocarbon content of the mixture depends upon the type of reactor utilized, its configuration and operating conditions. For example, it is expected that a lower hydrocarbon content will be obtained when operating a bubble column reactor with a slumped bed as opposed to operating it with a conventional dispersed bed reactor. The mixture withdrawn from the reactor may be initially treated by conventional techniques, for example by physical screening, to separate the fines from the remaining catalyst particles. Although the criteria for what are classified as fines particles may vary with the reactor, generally fines are recognized as particles smaller than 10 microns. These particles, which result from the turbulent conditions in the reactor, can be a problem as they tend to cause clogging of the reactor. The process of the prevent invention, by virtue of forming a melt, can renew fines that would otherwise be discarded or sent back to the manufacturer to be re-manufactured. The larger, useful catalyst particles separated from the fines may simply be returned to the reactor, or may be enhanced by slurry low temperature oxidation as described below prior to being returned to the reactor.

The catalyst-hydrocarbon mixture withdrawn from the reactor is initially treated to reduce its hydrocarbon content. This may be carried out by one or more of several techniques. For example, separation may be effected by gravitational or centrifugal separation which allows the hydrocarbon to be decanted or removed by filtration, all of which require the hydrocarbons to be in a fluid state. The mixture may also be treated with a solvent or supercritical fluid that effectively weakens the interaction of the hydrocarbon with the catalyst surface so that the liquid and solid phases can readily be separated in the same manner. Suitable solvents include, for example, paraffin solvents or naphthas, alcohols, and aromatic solvents. Supercritical fluids include, for example, carbon dioxide light paraffins and cyclopropane. Another means of reducing the hydrocarbon content of the mixture is to contact it with a hydrogen-containing gas at a temperature at least 20° C., preferably at least 50° C. higher than that of the reactor. The mixture may also be contacted with an oxygen-containing gas or steam at elevated temperature to effectively reduce the hydrocarbon content. A plurality of the foregoing methodologies for reducing the hydrocarbon content of the mixture may be utilized sequentially in any order.

A combination of the above-described steps is often necessary because the hydrocarbon product is both liquid and solid. For example, for a mixture containing from 1 to 50%, typically from 2 to 40%, of wax, physical separation, i.e. centrifugation/decanting or filtration to remove liquid hydrocarbon may advantageously be combined with treatment with hydrogen-containing gas at elevated temperature to dewax the catalyst particles. Typically, the hydrogen pressure would be from atmospheric to about 1000 psi, preferably from 10 to 400 psi. The duration of the dewaxing is adjusted to produce a residual carbon content of less than 5 wt. %, preferably less than 2 wt. %.

An alternative means of achieving a reduced hydrocarbon content mixture, or further processing the reduced hydrocarbon mixture formed above is by slurry low temperature oxidation wherein the mixture withdrawn from the reactor, or a slurry of the reduced hydrocarbon mixture in a suitable fluid is incompletely oxidized at low temperature to form an oxidized catalyst precursor comprising a mixture of metallic and oxidic species. By low temperature is meant a temperature below 200° C., preferably below 100° C. Typical oxidative gases in addition to oxygen include ozone and nitrogen oxides, i.e. nitrous oxide and nitric oxide. Soluble oxidants may be utilized as well and include, without intended limitation, dilute nitric acid, nitrates, for example, ammonium nitrate, hydrogen peroxide or art-recognized organic peroxides or hydroperoxides. Preferred solvents include, for example, water, mixtures of water and organic solvents, hydrocarbons, particularly those derived from the Fischer-Tropsch synthesis itself, or supercritical fluids such as carbon dioxide, liquid phase light hydrocarbons, i.e. C3–5 alkanes, cyclopentane and the like. Preferred mixed liquids include, without any intended limitation, mixtures or emulsions of water, hydrocarbons and lower alkanols. After this treatment, the catalyst particles are recovered by physical separation, i.e. gravitational or centrifugal separation, followed by filtration.

In accordance with the present invention, the reduced hydrocarbon mixture, or the mixture treated by slurry low temperature oxidation as described above, is converted to a DAM metal or metal alloy precursor. The first step in the conversion is heating above the melting point of at least one of the metals in a non-oxidizinig atmosphere, preferably a reducing atmosphere, for a time sufficient to form a melt. Those of ordinary skill in the art will appreciate that this heating step will remove substantially all of the non-metallic contaminants, such as carbon and sulfur, by the formation of volatile compounds. It will further he appreciated that this heating step is particularly advantageous to DAM catalysts that are substantially comprised of the metal or alloy themselves whereas, in contrast, such temperatures would be detrimental to conventional supported catalysts as their structure, morphology or physical integrity would be irreversibly destroyed. Any refractory metal oxides present can be separated or removed as a slag that floats on the surface of the melt. Other reducible metal contaminants, typically including but not limited to iron and nickel, that may have deposited on the surface of the catalyst, become redistributed into the bulk of the metal melt during the heating step, thus materially decreasing their concentration on the catalyst surface and, therefore, their detrimental effect. These metals, in the presence of carbon monoxide, have the capability to form metal carbonyls that have a negative effect on the efficacy of the catalyst. If an inordinately large amount of sulfur is present in the catalyst as a contaminant, methodologies common to the steel industry to enhance sulfur removal are typically employed. Such measures include the addition of a basic slag, for example, calcium oxide, calcium hydroxide, calcium carbonate, dolomite or, preferably, calcium magnesium silicate. A slag fluidity enhancer, such as calcium fluoride, may be added to enhance sulfur removal as well as the removal of refractory oxides. Temperatures in the range of 1,500–1,600° C. may further enhance the purification process.

The melt is then cooled and/or quenched by methods well known in the art to form a solid mass which is then treated to reduce the particle size thereof to a fine powder of renewed catalyst. For metal-hydride derived DAM catalysts, this is carried out by conventional multiple hydrogen absorption/desorption cycles. Those skilled in the art recognize that hydrogen absorption/desorption cycles applied to the metal hydride catalyst fulfill simultaneously both the requirements for dividing it into a fine powder and obtaining a metal hydride, corresponding to the DAM catalyst.

Wherein the DAM catalyst is a Raney type, e.g. a cobalt catalyst, a leachable metal such as aluminum, titanium, silicon or zinc, preferably aluminum, is added to the melt under a non-oxidizing atmosphere and the temperature maintained for a time sufficient to assure thorough mixing of the melt. Alternatively, metallic aluminum can be added to the mixture withdrawn from the reactor, or the reduced hydrocarbon mixture and the resulting mixture ignited, such as with an oxy-flame or electrical arc, to form a DAM metal or metal alloy precursor and a slag as described above which can be removed before further processing. In a preferred embodiment, the leachable metal is added to the reduced hydrocarbon content mixture prior to forming the melt. Following, removal of any slag that has formed, the melt is cooled or quenched as above. The resulting solid is then treated by physical comminuting, i.e. crushing or grinding, to a reduced particle size, typically having an average particle size of from about 1 to 500 microns, preferably from 20 to 150 microns. The renewed Raney metal or DAM catalyst is then obtained by extraction of the leachable metal with alkali, preferably a concentrated aqueous solution of sodium hydroxide. Any of the various extraction methods available in the literature may be utilized to remove the leachable metal. Any fines resulting from the comminuting step are removed by physical separation, i.e. screening, and can be recycled to a subsequent melt.

The renewed DAM catalyst particles have a significant portion, i.e. in excess of about 80%, of their original activity renewed are then returned to the reactor as described above. This may be carried out by forming a slurry of the DAM particles in liquid hydrocarbon, conveniently the hydrocarbon mixture withdrawn from the reactor to initiate the process from which the catalyst has been separated, or by suspending the particles in a non-oxidizing gas, preferably a reducing gas, or by gravity or pressure gradient, or any combination thereof.

It is within the scope of the present invention to further enhance the catalyst prior to returning it to the reactor by slurry low temperature oxidation as described above to form an oxidized catalyst precursor that is a mixture of metallic and oxidic species. The oxidized catalyst precursor particles are treated to reform the active catalyst by reduction with hydrogen-containing gas at temperatures of from about 200° C. to 600° C., preferably from about 300° C. to 450° C., most preferably from about 340° C. to 400° C. Hydrogen partial pressure during the reduction would range from about 1 to 100 atmospheres, preferably from about 1 to 40 atmospheres. The active DAM catalyst particles are then returned to the reactor.

It is within the scope of the present invention to passivate the renewed or enhanced catalyst particles before returning them to the hydrocarbon synthesis reactor. The passivation may be carried out by contacting the catalyst particles with a gas containing carbon monoxide, or carbon monoxide and hydrogen, under conditions such that carbon monoxide does not significantly decompose and is not hydrogenated to a material degree. Such conditions, for example, would be a temperature below about 150° C., preferably between about 25° C. and 100° C., and pressure below about 20 atm, particularly between about 1 and 10 atm. Those of ordinary skill in the art will appreciate that some decomposition or hydrogenation, respectively, of the carbon monoxide may take place regardless of the precautions taken by the operator. Hence, by "significantly" is meant that such decomposition/hydrogenation does not exceed 5% by volume of the feed gas. It has been found that catalysts that have been passivated in this manner typically exhibit higher initial carbon monoxide hydrogenation activity than similar, but unpassivated, catalysts. This passivation treatment may be carried out on renewed catalysts or catalysts that have been enhanced as will be described below. Other passivating agents include, for example, traces of oxygen or carbon dioxide.

It is within the scope of the present invention to not only renew the DAM catalyst withdrawn from the reactor, but to modify and/or enhance the properties thereof. This may be effected by the addition of one or more metal or metal compounds chosen among, without limitation, those active for carbon monoxide hydrogenation per se or for promoting either the activity or the selectivity of the catalyst. Suitable metals include, for example, Group VIII metals, Mo, W, Cu, Si, Cr, Ti, Mg, Mn, Zn, Hf, Al, Th and the like. The metal or metal compounds may be added before or after the formation of the melt as described above.

It is understood that various other embodiments and modifications in the practice of the invention will be apparent to, and can be readily made by, those of ordinary skill in the art without departing form the scope and spirit of the invention as described above. For example, although the process has been described in terms of being integrated into a Fischer-Tropsch synthesis to renew and return DAM catalyst particles during operation of a reactor, the process can be utilized as a stand-alone operation as well. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the art to which the invention pertains. The invention is further described with reference to the following experimental work.

EXAMPLE 1
Slurry Low Temperature Oxidation

A slurry of Raney cobalt catalyst consisting of about 1 lb Co with water wherein the volume ratio of water to cobalt was at least 5:1 was placed in a round bottom flask. The Raney cobalt was stirred into suspension with a glass stirrer. A total of 300 ml of 0.5N nitric acid was added drop-wise. During the addition, the temperature of the slurry slowly rose to about 50° C. and the pH increased to about 11. During the oxidation of the catalyst, the nitrate ions are reduced to ammonium ions, hence the basic pH. The total amount of nitrate ions added was adjusted in order to achieve a complete consumption of the hydrogen dissolved in the Raney catalyst and the native hydrogen generated by the acidic oxidation of the metal. Further addition of nitric acid would result in a lowering of the pH and dissolution of Co ions in the water as indicated by a pink color, which is undesirable. After stirring for five minutes, the solids were filtered, washed four times with deionized water and dried in a vacuum oven at 80° C. for two hours. The oxidized catalyst was stored as made.

Thermogravimetric analysis of the catalyst showed that, in contrast to a complete oxidation with air at 700° C. (which produces pure $Co_3O_4$), a stoichiometry of one oxygen per Co was found. The conventionally treated catalyst of pure $Co_3O_4$ has stoichiometry of 1.33 oxygen per Co. X-ray diffraction analysis showed that the oxidized catalyst was composed of cobalt metal, CoO, $Co(OH)_2$ and $Co_3O_4$.

EXAMPLE 2
Preparation of a Wax-coated Oxidized Catalyst

This example describes the preparation of a catalyst that simulates the composition of a catalyst containing significant contaminants that would be recovered from a slurry reactor which had been running for a substantial period of time. A sample of the oxidized catalyst prepared in Example 1 was slurried in hot Fischer-Tropsch wax and allowed to settle. Upon cooling, the bottom section of the resulting solid cylinder, where the catalyst had settled, was removed and the wax remelted. The thin layer of wax that formed on the surface was removed by scraping. This process was repeated twice more until no significant layer of wax formed in the top of the catalyst. The wax-coated catalyst contained 20 wt % wax, as measured by weight gain.

EXAMPLE 3
Dewaxing of the Wax-Coated Catalyst

A sample of the wax-coated catalyst prepared in Example 2, was treated under flowing hydrogen (100 cc/min, 1 atm) at 600° C. for about eight hours. The resulting material was transferred to an electron microscope under an inert atmosphere. Microscopy and compositional analysis by Energy Dispersive X-ray showed that the carbon was effectively removed (<0.1 wt %) and the cobalt reduced to its metallic state (<0.1 wt % Oxygen). This example demonstrates that pure cobalt metal can be recovered from an oxidized, wax-covered catalyst.

EXAMPLE 4
Removal of Refractory Oxides

A sample of $Co_3O_4$ and aluminum powder were mixed in stoichiometric amounts and placed in a crucible. The crucible was in turn placed in a furnace and purged with argon. The mixture was electrically ignited by remote control to trigger an aluminothermic reaction. The temperature increased very rapidly to about 5,000° F. Upon cooling, a metallic ingot of pure cobalt was formed. On the top surface of the metallic ingot there was a blue slag of cobalt doped alumina. Compositional analysis showed that the ingot was pure cobalt metal and that the slag was an alumina containing less that 4 ppm of cobalt. During the intense heating, the large difference in density between the cobalt metal and the alumina resulted in the separation of the two phases. This example shows that contaminants forming phases other than pure metal or alloy phases will form a low-density slag, which will readily separate from the metallic or alloy phase.

EXAMPLE 5
Direct Preparation of a CoAl Alloy

A mixture of $Co_3O_4$ and wax-coated catalyst in a ratio of 3:1 was mixed with a stoichiometric amount of aluminum powder and placed into a crucible. Under of continuous flow of argon, the mixture was ignited electrically by remote control to initiate the reaction. The reaction occurred with some degree of explosive intensity, due to the rapid gasification of the carbonaceous matter present in the mixture. Because of the extent of reaction intensity, some products escaped from the crucible, but not enough so that compositional and characterization analysis could not be carried out. The results of such analysis indicate that a Co—Al alloy was formed which consisted of 83.48 atomic % of Co and 16.52 wt % of aluminum. No carbon was detected. Because a stoichiometric amount of aluminum was utilized, the formation of CoAl alloy suggests that some of the oxygen contained in the catalyst was consumed as carbon oxides, hence resulting in an excess of Al. This example shows that deactivated catalyst containing carbon and oxygen can be directly converted to a Raney alloy.

What is claimed is:

1. A process for the catalytic hydrogenation of carbon monoxide to form a mixture of hydrocarbons in a reactor utilizing a catalyst that is a Dispersed Metal Catalyst (DAM) and is not immobilized, said catalyst comprising one or one or more members selected from the group consisting of Group VIII metals and copper, the process including renewing the catalyst during operation of the reactor to produce said hydrocarbons by the following steps:

a) withdrawing a mixture comprising hydrocarbons and a portion of said catalyst from the reactor;

b) treating said mixture to reduce the hydrocarbon content thereof;

c) heating the resulting mixture in a non-oxidizing atmosphere to a temperature above the melting temperature of at least one of said metals thereby substantially removing non-metallic impurities therefrom and forming a slag of any refractory metal oxides therein on the resulting melt;

d) removing the slag, if present;

e) cooling the melt to solidify it;

f) treating the solid to reduce the particle size thereof to a fine powder of renewed catalyst; and g) returning the catalyst to the reactor.

2. A process in accordance with claim 1, wherein the mixture withdrawn from the reactor is treated to reduce the hydrocarbon content there by one or a plurality, in any sequence, of the following steps:

gravitational or centrifugal separation of the catalyst particles from the hydrocarbons and decanting the hydrocarbons therefrom filtration of the mixture;

treating the mixture with a solvent or supercritical fluid that weakens the interaction between the particles and the hydrocarbons, followed by separation of the liquid and solid phases:

contacting the mixture with a hydrogen-containing gas at a temperature above that required for the carbon monoxide hydrogenation; and contacting the mixture with an oxygen-containing gas or steam at elevated temperature.

3. A process in accordance with claim 1, wherein the catalyst in the mixture withdrawn from the reactor in step a) or the reduced hydrocarbon mixture resulting from step b) is incompletely oxidized at low temperature in a slurry with a suitable fluid to form a mixture of metallic and oxidic species which is then heated in step c).

4. A process in accordance with claim 3, wherein the mixture is oxidized with a gaseous oxidant selected from the group consisting of oxygen, ozone and nitrogen oxides.

5. A process in accordance with claim 1, wherein in step c) removal of sulfur contaminants from the mixture is enhanced by the addition thereto of a basic slag.

6. A process in accordance with claim 1, wherein in step c) removal of refractory oxides from the mixture is enhanced by the addition thereto of calcium fluoride.

7. A process in accordance with claim 1, wherein the particle size of the solid formed in step e) is reduced by a plurality of hydrogen absorption/desorption cycles.

8. A process in accordance with claim 1, wherein the catalyst is returned to the reactor by one or more of:

forming a slurry of the catalyst with liquid hydrocarbons and introducing said slurry into the reactor;

forming a suspension of the catalyst in a non-oxidizing gas and introducing said suspension into the reactor; or transferring the catalyst to the reactor by gravity or pressure gradient.

9. A process in accordance with claim 1, wherein, prior to being returned to the reactor the activity of the catalyst is further enhanced by a process comprising:

forming a slurry of the catalyst particles in a suitable liquid;

contacting the catalyst with an oxidizing agent at temperatures below 200° C. thereby forming an oxidized catalyst precursor comprising said metals and at least one of hydroxides and oxides thereof, and reducing said oxidized catalyst precursor with a hydrogen-containing gas at a temperature above about 200° C.

10. A process in accordance with claim 9, wherein said oxidized catalyst precursor is reduced with hydrogen-containing gas at a temperature above about 300° C.

11. A process in accordance with claim 1, further including the step of modifying or enhancing the activity of the renewed catalyst by adding one or more metals selected from the group consisting of Re, Ru, Co, Pt, Pd, Mo, W, Cr, Ni, Mg, Zr, Hf, Mn, Fe, Cu and Ce to the reduced hydrocarbon mixture formed in step b) or the melt formed in step c).

12. A process in accordance with claim 8 wherein, prior to being reintroduced into the reactor, the catalyst is passivated by:

treatment with a carbon monoxide-containing, gas under conditions such that the carbon monoxide is not significantly decomposed; or treatment with a gas containing carbon monoxide and hydrogen under conditions such that the carbon monoxide is not significantly hydrogenated.

13. A process in accordance with claim 1, wherein said DAM catalyst is withdrawn and replaced periodically during operation of the reactor.

14. A process in accordance with claim 1, wherein said DAM catalyst is withdrawn and replaced continuously during operation of the reactor.

15. A process in accordance with claim 1, wherein the catalyst particles withdrawn in step a) are physically separated to separate fines particles therefrom and only said fines particles are processed in step b).

16. A process in accordance with claim 1, wherein the DAM catalyst is a Raney catalyst, said process additionally including the steps of adding a leachable metal selected from the group consisting of aluminum, titanium silicon or zinc to the reduced hydrocarbon mixture formed in step b) or the melt formed in step c), and the solid formed in step e) is reduced to a fine powder of renewed catalyst by physical comminuting to reduce the particle size followed by chemical extraction or dissolution of said leachable metal.

17. A process in accordance with claim 16, wherein, prior to being returned to the reactor, the activity of the catalyst is further enhanced by a process comprising:

forming a slurry of the catalyst particles in a suitable liquid;

contacting the catalyst with an oxidizing agent at temperatures below 200° C. for thereby forming an oxidized catalyst precursor comprising metals and at least one of hydroxides thereof and oxides thereof, and reducing said oxidized catalyst precursor with a hydrogen-containing gas at a temperature above about 200° C.

18. A process in accordance with claim 17, wherein said oxidized catalyst precursor is reduced with hydrogen-containing gas at a temperature above about 300° C.

19. A process in accordance with claim 16, further including the step of modifying or enhancing the activity of the renewed catalyst by adding one or more metals selected from the group consisting of Re, Ru, Co, Pt, Pd, Mo, W, Cr, Ni, Mg, Zr, Hf, Mn, Fe, Cu and Ce to the reduced hydrocarbon mixture formed in step b) or the melt formed in step c).

20. A process in accordance with claim 16, wherein the renewed catalyst is returned to the reactor by one or more of:

forming a slurry of the catalyst with liquid hydrocarbons and introducing said slurry into the reactor;

forming a suspension of the catalyst in a non-oxidizing gas and introducing said suspension into the reactor; or transferring the catalyst to the reactor by gravity or pressure gradient.

21. A process in accordance with claim 20, wherein, prior to being reintroduced into the reactor, the catalyst is passivated by:

treatment with a carbon monoxide-containing gas under conditions such that the carbon dioxide is not significantly decomposed; or treatment with a gas containing carbon monoxide and hydrogen under conditions such that the carbon monoxide is not significantly hydrogenated.

22. A process in accordance with claim 1, wherein the catalyst particles withdrawn in step a) are physically separated to separate fines particles therefrom and only said fines particles are process in step b).

23. A renewed Dispersed Active Metal catalyst formed during the production of a mixture of hydrocarbons by catalytic hydrogenation of carbon monoxide in a reactor wherein the catalyst is not immobilized, said catalyst comprising one or one or more members selected from the group consisting of Group VIII metals and copper, said catalyst being formed by:

a) withdrawing a mixture comprising hydrocarbons and a portion of said catalyst from the reactor;

b) treating said mixture to reduce the hydrocarbon content thereof;

c) heating the resulting mixture in a non-oxidizing atmosphere to a temperature above the melting temperature of at least one of said metals thereby substantially removing non-metallic impurities therefrom and forming a slag of any refractory metal oxides therein on the resulting melt;

d) removing the slag, if present;

e) cooling the melt to solidify it; and f) treating the solid to reduce the particle size thereof to a fine powder of renewed catalyst.

24. A renewed Dispersed Active Metal catalyst in accordance with claim 23, wherein the activity thereof is further enhanced by a process comprising:

forming a slurry of the renewed catalyst particles in a suitable liquid;

contacting the catalyst with an oxidizing agent at temperatures below 200° C. for thereby forming an oxidized catalyst precursor comprising metals and at least one of hydroxides thereof and oxides thereof, and reducing said oxidized catalyst precursor with a hydrogen-containing gas at a temperature above about 200° C.

25. A renewed DAM catalyst in accordance with claim 23, wherein the DAM catalyst is a Raney catalyst, said process additionally including the steps of adding a leachable metal selected from the group consisting of aluminum, titanium, silicon or zinc to the reduced hydrocarbon mixture formed in step b) or the melt formed in step c), and the solid formed in step c) is reduced to a fine powder of renewed catalyst by physical comminuting to reduce the particle size followed by chemical extraction or dissolution of said leachable metal.

26. A catalyst in accordance with claim 23 comprising a plurality of metals, wherein one of said metals is cobalt.

27. A process for producing higher hydrocarbons by the hydrogenation of carbon monoxide by reaction with hydrogen at reaction conditions in the presence of an renewed catalyst according to claim 1.

28. A process in accordance with claim 27, wherein at least a portion of the hydrocarbons formed are upgraded to more valuable products by at least one of fractionation and conversion operations.

29. A process for producing higher hydrocarbons by the hydrogenation of carbon monoxide by reaction with hydrogen at reaction conditions in the presence of a renewed, enhanced catalyst according to claim 16.

30. A process in accordance with claim 29, wherein said metals are cobalt, or a combination of cobalt and a minor quantity of a metal that is a promoter for the catalytic activity thereof in the hydrogenation process.

31. A process in accordance with claim 30, wherein at least a portion of the hydrocarbons formed are upgraded to more valuable products by at least one of fractionation and conversion operations.

* * * * *